United States Patent
Laroche et al.

(10) Patent No.: US 10,940,458 B2
(45) Date of Patent: Mar. 9, 2021

(54) ZEOLITE ADSORBENT IN THE FORM OF LOW-TORTUOSITY AGGLOMERATES

(71) Applicants: IFP Energies Nouvelles, Rueil-Malmaison (FR); Arkema France, Colombes (FR)

(72) Inventors: Catherine Laroche, Vernaison (FR); Philibert Leflaive, Mions (FR); Ludivine Bouvier, Orthez (FR); Cécile Lutz, Gan (FR)

(73) Assignees: IFP ENERGIES NOUVELLES, Rueil-Malmaison (FR); ARKEMA FRANCE, Colombes (FR)

( * ) Notice: Subject to any disclaimer, the term of this patent is extended or adjusted under 35 U.S.C. 154(b) by 0 days.

(21) Appl. No.: 16/312,059

(22) PCT Filed: Jun. 28, 2017

(86) PCT No.: PCT/EP2017/066054
§ 371 (c)(1),
(2) Date: Dec. 20, 2018

(87) PCT Pub. No.: WO2018/002174
PCT Pub. Date: Jan. 4, 2018

(65) Prior Publication Data
US 2019/0160450 A1 May 30, 2019

(30) Foreign Application Priority Data
Jun. 28, 2016 (FR) ...................... 16 56031

(51) Int. Cl.
*B01J 20/18* (2006.01)
*B01J 20/28* (2006.01)
*B01J 20/30* (2006.01)
*C07C 7/13* (2006.01)
*B01J 35/10* (2006.01)
*B01D 15/18* (2006.01)
*B01D 15/08* (2006.01)
*B01J 37/30* (2006.01)
*C01B 39/02* (2006.01)
*C07C 15/08* (2006.01)

(52) U.S. Cl.
CPC ............ *B01J 20/186* (2013.01); *B01D 15/08* (2013.01); *B01D 15/185* (2013.01); *B01D 15/1821* (2013.01); *B01J 20/18* (2013.01); *B01J 20/28* (2013.01); *B01J 20/2803* (2013.01); *B01J 20/28004* (2013.01); *B01J 20/28007* (2013.01); *B01J 20/2808* (2013.01); *B01J 20/28011* (2013.01); *B01J 20/28054* (2013.01); *B01J 20/28092* (2013.01); *B01J 20/3028* (2013.01); *B01J 20/3071* (2013.01); *B01J 20/3085* (2013.01); *B01J 35/10* (2013.01); *B01J 35/108* (2013.01); *B01J 35/109* (2013.01); *B01J 35/1033* (2013.01); *B01J 35/1052* (2013.01); *B01J 35/1095* (2013.01); *B01J 37/30* (2013.01); *C01B 39/026* (2013.01); *C07C 7/13* (2013.01); *C07C 15/08* (2013.01)

(58) Field of Classification Search
CPC . B01J 20/18; B01J 20/186; B01J 20/28; B01J 20/28092; B01J 20/3028; B01J 20/2808; B01J 20/28004; B01J 20/28011; B01J 20/28054; B01J 20/2803; B01J 20/3085; B01J 20/3071; B01J 20/28007; B01J 35/10; B01J 35/108; B01J 35/1095; B01J 35/109; B01J 35/1052; B01J 35/1033; B01J 37/30; C07C 7/13; C07C 15/08; B01D 15/08; B01D 15/185; B01D 15/1821; C01B 39/026
USPC ............. 502/60, 79, 85, 400, 411, 414, 407; 585/828, 826, 820, 805, 804; 423/710, 423/709
See application file for complete search history.

(56) References Cited

U.S. PATENT DOCUMENTS

| | | | |
|---|---|---|---|
| 6,410,815 B1 | 6/2002 | Plee et al. | |
| 6,425,940 B1 | 7/2002 | Chao et al. | |
| 8,735,643 B2 | 5/2014 | Bouvier et al. | |
| 9,050,581 B2 | 6/2015 | Bouvier et al. | |
| 9,707,539 B2 * | 7/2017 | Bats ...................... | B82Y 30/00 |
| 10,112,173 B2 | 10/2018 | Bouvier et al. | |
| 2009/0326309 A1 | 12/2009 | Priegnitz et al. | |

(Continued)

FOREIGN PATENT DOCUMENTS

| | | |
|---|---|---|
| FR | 3004966 A1 | 10/2014 |
| IN | 2738MUM2014 A | 4/2016 |

(Continued)

OTHER PUBLICATIONS

Carniglia, S.C., "Construction of the Tortuosity Factor from Porosimetry," 1986, vol. 102, pp. 401-418, Journal of Catalysis.

(Continued)

Primary Examiner — Elizabeth D Wood
(74) Attorney, Agent, or Firm — RatnerPrestia

(57) ABSTRACT

Provided is a zeolite-based adsorbent in the form of agglomerates, where the adsorbent having a tortuosity factor, calculated from the pore distribution determined by mercury intrusion porosimetry, of greater than 1 and less than 3. The adsorbent also has a porosity as determined by mercury intrusion porosimetry of between 25% and 35%. The adsorbent is useful in the field of separations in particular in a process for separating para-xylene from aromatic hydrocarbon isomer fractions containing 8 carbon atoms.

16 Claims, No Drawings

(56) References Cited

U.S. PATENT DOCUMENTS

| | | | |
|---|---|---|---|
| 2011/0105301 A1* | 5/2011 | Wang | B01J 20/183 502/62 |
| 2016/0067673 A1* | 3/2016 | Bats | B82Y 30/00 568/751 |
| 2016/0289146 A1 | 10/2016 | Laroche et al. | |
| 2017/0304799 A1* | 10/2017 | Bouvier | B01J 20/28059 |

FOREIGN PATENT DOCUMENTS

| | | |
|---|---|---|
| WO | 9910096 A1 | 3/1999 |
| WO | 2009081024 A2 | 7/2009 |
| WO | 2015075140 A1 | 5/2015 |
| WO | 2016075280 A1 | 5/2016 |

OTHER PUBLICATIONS

Kärger et al., "Diffusion in Nanoporous Materials", vol. 1, published by Wiley, 2012, p. 95-96.

Breck, D., "Zeolites Molecular Sieves", John Wiley & Sons, 1973—4 pages.

International Search Report and Written Opinion for Application No. PCT/EP/2017/066054, dated Sep. 25, 2017—11 pages.

Ruthven et al., "Principles of Adsorption and Adsorption Processes", John Wiley & Sons, 1984, pp. 124, 248-250, and 326-407—453 pages.

Win, P., "Preparation of Synthetic Zeolites from Myanmar Clay Mineral", International Nuclear Information System (INIS) IAEA, Apr. 1, 2004—pp. 1-29.

Rasouli et al., "Para-Xylene Adsorption Separation Process Using Nano-Zeolite Ba-X", Chemical Engineering Research and Design, 2014, vol. 92, pp. 1192-1199.

Iranian Search Report and Written Opinion for Iranian Application No. 139750140003008464, dated Oct. 2019 with translation, 10 pages.

Tanko, N.L., "The effect of Porosity on Tortuosity," May 1, 2018, pp. 2163-2169, vol. 9, Issue 5, International Journal of Scientific & Engineering Research.

European Communication pursuant to Article 94(3) for European Application No. 17 732 476.1, dated Apr. 9, 2020, 9 pages.

Singapore Search Report for Singapore Application No. 11201811720R, dated Mar. 3, 2020, 9 pages.

Indian Examination Report for Indian Application No. 20181704839, dated Dec. 11, 2020, with translation; 6 pages.

* cited by examiner

ZEOLITE ADSORBENT IN THE FORM OF LOW-TORTUOSITY AGGLOMERATES

CROSS-REFERENCE TO RELATED APPLICATIONS

This is the national phase of International Application No. PCT/EP2017/066054, filed Jun. 28, 2017, which claims priority to French Application No. 1656031, filed Jun. 28, 2016. The disclosure of each of these applications is incorporated herein by reference in its entirety for all purposes.

FIELD OF THE INVENTION

The present invention relates to the field of adsorbents of zeolite structure and more particularly to the field of adsorbents of zeolite structure in the form of agglomerates. The present invention also relates to the preparation of said agglomerates of zeolite structure, and also to the uses thereof for the separation of gaseous or liquid mixtures.

DESCRIPTION OF THE BACKGROUND

The synthesis of zeolites leads to crystals, generally in powder form, whose use at the industrial scale is particularly difficult. Specifically, it is known at the present time how to synthesize zeolite crystals with sizes ranging from a few nanometres to a few micrometres, which are sizes required to give zeolites optimum adsorption capacities. There are, however, numerous drawbacks associated with these small crystals, among which drawbacks mention may be made of the difficulty in handling pulverulent powder and the large losses of pressure during their use.

In order to overcome these drawbacks, it has thus been proposed to use agglomerated forms of these crystals, for example in the form of spun yarns, beads and other agglomerated forms. The manufacture of such agglomerates from zeolite crystals in powder form is nowadays well known, and the scientific literature and patent literature provide numerous examples of preparation of zeolite-based agglomerates, especially by extrusion, pelletizing and other agglomeration techniques known to those skilled in the art.

These agglomerates usually have sizes of the order of a few tens of micrometres, or even of a few hundred micrometres, or even of a few millimetres, and do not have the drawbacks inherent in the zeolite crystal pulverulent materials defined previously.

These agglomerates, whether they are in the form of platelets, beads, extrudates or the like, are generally constituted of zeolite crystals, which constitute the active element (in the sense of adsorption) and an agglomeration binder.

This agglomeration binder is intended to ensure the cohesion of the crystals to each other in the agglomerated structure, but must also give said agglomerates sufficient mechanical strength so as to prevent, or at the very least minimize, the risks of fractures, splitting or breaks that may arise during their industrial uses during which the agglomerates are subjected to numerous constraints, such as vibrations, high and/or frequent pressure variations, movements and the like. It is thus very important for the zeolite-based agglomerates subjected to these various constraints to remain cohesive and not to generate fine pulverulent particles leading to the abovementioned drawbacks. It is thus very important to have available zeolite-based agglomerates that have improved properties, especially such as improved stability over time, i.e. agglomerates whose separation performance qualities over time are not deteriorated.

However, the adsorption properties of these agglomerates are obviously reduced relative to the crystal powder due to the presence of agglomeration binder which is inert with respect to adsorption.

Various means have already been proposed for overcoming this drawback of the agglomeration binder being inert as regards the adsorption performance, among which is the transformation of all or at least part of the agglomeration binder into zeolite that is active from the adsorption viewpoint. This operation is now well known to those skilled in the art, for example under the name "zeolitization". To perform this operation readily, zeolitizable binders are used, usually clays belonging to the kaolinite family, and preferably precalcined at temperatures generally between 500° C. and 700° C., i.e. at temperatures directed toward firing the clay.

The main factors that influence the performance qualities of an adsorption separation process especially include the adsorption selectivity, the adsorption capacity and the mass transfer kinetics within the adsorbent which controls the rates of adsorption and desorption of the various compounds. The adsorbent must thus have good mass transfer properties so as to ensure a sufficient number of theoretical plates to perform efficient separation of the species in admixture, as indicated by Ruthven in the book entitled *Principles of Adsorption and Adsorption Processes*, John Wiley & Sons, (1984), pages 326 and 407. To estimate the improvement in transfer kinetics, it is possible to use the plate theory described in the cited publication, on pages 248-250. This approach is based on the representation of a column by a finite number of ideally stirred hypothetical reactors (theoretical stages). The equivalent height of theoretical plates is a direct measurement of the axial dispersion and of the resistance to mass transfer of the system.

Ruthven states (ibid., page 124) that, in general, the transportation of molecules to the core of the porous network of the adsorbent takes place not by flow, but by diffusion. The mechanism of diffusion into the porous network depends especially on the size of the pores, and consequently, within the adsorbent constituted of agglomerated zeolite crystals, two diffusion regimes coexist: intra-crystalline diffusion in the zeolite micropores, and intra-particulate diffusion in the macropores and mesopores of the inter-crystalline space. The overall transfer time within a zeolite-based adsorbent in the form of agglomerates will then be the addition of the time of transfer by intra-particulate diffusion through the macroporous and mesoporous network and the time of transfer by intra-crystalline diffusion. Now, the characteristic time of transfer by diffusion within a particle of spherical geometry is generally written as the square of the radius of the particle divided by the diffusivity of the molecules transported within this particle. Consequently, for the purpose of improving the mass transfer within zeolite-based adsorbents in the form of agglomerates, it will be sought first and foremost to reduce the size of the zeolite crystals and/or the size of the agglomerates.

In practice, it will be sought to reduce the size of the agglomerates, but only up to a certain point, since this parameter determines the loss of pressure and the uniformity of filling within the industrial unit during the use of the adsorbent in the industrial application.

Similarly, reducing the size of the crystals makes it possible to improve the micropore transfer, but would run the risk of having an effect on the intra-particulate diffusivity in the macropores. Consequently, it is not desirable to excessively reduce the size of the crystals, so as not to risk unacceptably reducing the intra-particulate diffusivity. Other routes for improving the transfer thus remain to be investigated.

When molecules diffuse through a porous material, their effective diffusivity through the porous network $D_p$ is reduced relative to their diffusivity $D_0$ when they diffuse in an open volume. The reduction factor is equal to the ratio of the porosity $\varepsilon_p$ with the tortuosity factor $\tau$ of the porous material, according to equation 1 (publication by Kärger, Ruthven and Theodorou, "Diffusion in Nanoporous Materials", Volume 1, published by Wiley, 2012, page 95):

$$\frac{D_p}{D_0} = \frac{\varepsilon_p}{\tau} \qquad \text{Equation 1}$$

A high porosity factor $\varepsilon_p$ value, of macroporosity and/or mesoporosity type, thus favors diffusion. However, it is not desirable to greatly increase the macroporosity and/or mesoporosity, since this porosity does not participate in the adsorption capacity. Consequently, a person skilled in the art will not seek to increase it for the purpose of reducing the intra-particulate diffusion time in the macropores and mesopores of the inter-crystalline space, given that this would take place to the detriment of the volume adsorption capacity.

The tortuosity factor $\tau$ is a property of the adsorbent and does not depend on the diffusing molecule. This factor $\tau$ takes into account the diffusion length when the molecules diffuse through a three-dimensional porous space constituted of pores that are interconnected via restrictions, relative to rectilinear cylindrical pores with the same mean pore diameter. Kärger states (ibid., page 96) that the tortuosity factor $\tau$ values measured experimentally are typically between 2 and 5.

Optimum diffusion properties (i.e. optimum mass transfer), optimum adsorption capacities, while at the same time conserving maximum mechanical strength for adsorbents of zeolite structure in the form of agglomerates were obtained by specifically selecting both the porosity and the tortuosity factor.

SUMMARY OF THE INVENTION

A first object of the present invention is thus to propose zeolite-based adsorbents in the form of agglomerates with optimized properties for the separation of gaseous or liquid mixtures of isomers and more particularly for the gas-phase or liquid-phase separation of xylenes, especially of para-xylene from C8 aromatic fractions. The zeolite-based adsorbents of the invention especially have maximum selectivity properties for para-xylene and maximum mass transfer properties, while at the same time having improved strength and a high adsorption capacity per unit volume of adsorbent, and are particularly suitable for use in a process for the liquid-phase separation of para-xylene, preferably of simulated counter-current type.

The invention relates to a zeolite-based adsorbent in the form of agglomerates, said adsorbent having:

a tortuosity factor $\tau$, calculated from the pore distribution determined by mercury intrusion porosimetry, strictly greater than 1 and strictly less than 3;

a porosity $$\varepsilon_p = \frac{Vma + Vme}{Vg},$$

determined by mercury intrusion porosimetry, in which $V_{ma}$ denotes the macropore volume, $V_{me}$ denotes the mesopore volume and Vg denotes the grain volume, of between 25% and 35%, the volumes being expressed in $cm^3 \cdot g^{-1}$.

Preferably, the tortuosity factor $\tau$ is between 1.5 and 2.7.

The high mechanical bulk crushing strength (BCS), measured via the Shell method series SMS1471-74 adapted for agglomerates less than 1.6 mm in size, is generally greater than or equal to 1.0 MPa.

Said adsorbent advantageously has a size of between 0.1 mm and 1 mm, limits inclusive.

Said adsorbent may comprise a zeolite chosen from zeolites of FAU structure, preferably zeolite X, alone or as a mixture with other zeolites.

Said adsorbent may comprise more than 90% by weight of zeolite(s).

Said zeolite(s) are advantageously in the form of crystals between 10 nm and 1500 nm in size. Preferably, the pore distribution satisfies the inequalities a) and/or b) below:

$$\frac{Vme}{Vme + Vma} \leq 0.1, \qquad \text{a)}$$

$$0.4 \leq \frac{Vmi}{Vma + Vme + Vmi}. \qquad \text{b)}$$

Vmi denoting the micropore volume expressed in $cm^3 \cdot g^{-1}$, determined by nitrogen adsorption.

The zeolite-based adsorbent may also comprise barium and/or potassium.

The invention also relates to a process for preparing said zeolite-based adsorbent, comprising at least the following steps:

a) a step of mixing crystals of at least one zeolite with an agglomeration binder containing at least 80%, preferably at least 90% and more preferably at least 95% by weight of zeolitizable clay, and optionally a source of silica, followed by forming and firing the agglomerates at a temperature of between 500 and 700° C.;

b1) a first step of zeolitization by placing the zeolite-based agglomerates obtained in step a) in contact with an alkaline basic solution, with a concentration of between 0.2 M and 0.9 M, limits inclusive;

b2) a second step of zeolitization by placing the zeolite-based agglomerates obtained in step b1) in contact with an alkaline basic solution, with a concentration of between 1.2 M and 4.0 M, limits inclusive;

b1 and b2 possibly being performed in any order and b1 and/or b2 possibly being repeated;

c) an optional step of cationic exchange of the cations contained in the reaction medium obtained from the zeolitization steps by placing in contact with a solution of barium ions or of barium ions and potassium ions;

d) a step of washing and drying the zeolite-based agglomerates thus obtained; and e) a step of activation by heating to a temperature of between 100° C. and 400° C. of the zeolite-based adsorbent in the form of agglomerates obtained in step d).

The process may comprise one or more additional forming steps performed after any one of steps a), b1)/b2), c), d) or e).

The invention also relates to a process for separating para-xylene from aromatic hydrocarbon isomer fractions containing 8 carbon atoms, in the liquid phase, by absorption of para-xylene using said adsorbent or an adsorbent that may be prepared according to the preparation process in the presence of a desorbent.

The invention also relates to a process for separating para-xylene from aromatic hydrocarbon isomer fractions containing 8 carbon atoms, in the gaseous phase, by adsorption of the para-xylene using said adsorbent or an adsorbent that may be prepared according to the preparation process in the presence of a desorbent.

Said separation process may be of the simulated moving bed type.

DETAILED DESCRIPTION OF THE INVENTION

The zeolite-based adsorbent in the form of agglomerates of the invention comprises macropores, mesopores and also micropores. The term "macropores" means pores whose aperture is greater than 50 nm. The term "mesopores" means pores whose aperture is between 2 nm and 50 nm, limits not inclusive. The term "micropores" means pores whose aperture is less than 2 nm, typically strictly greater than 0 and less than or equal to 2 nm.

In the description of the present invention, the term "pore distribution" means the distribution of the pore volume as a function of the pore diameter.

Moreover, the term "Vma" denotes the macropore volume expressed in $cm^3 \cdot g^{-1}$ of adsorbent, the term "Vme" denotes the mesopore volume expressed in $cm^3 \cdot g^{-1}$ of adsorbent, and the term "Vmi" denotes the micropore volume expressed in $cm^3 \cdot g^{-1}$ of adsorbent.

The term "Vg" represents the grain volume of the adsorbent expressed in $cm^3 \cdot g^{-1}$ of adsorbent.

More precisely, the present invention relates to a zeolite-based adsorbent in the form of agglomerates, said adsorbent having:

a tortuosity factor τ, calculated from the pore distribution determined by mercury intrusion porosimetry, strictly greater than 1 and strictly less than 3, preferably between 1.5 and 2.7;

a porosity $$\varepsilon_p = \frac{Vma + Vme}{Vg},$$

determined by mercury intrusion porosimetry, in which Vma denotes the macropore volume, Vme denotes the mesopore volume and Vg denotes the grain volume, of between 25% and 35%, the volumes being expressed in $cm^3 \cdot g^{-1}$.

In the description of the invention, the term "size" means the number-mean diameter of an object, or its number-mean largest dimension when it is not spherical. The zeolite-based adsorbent in the form of agglomerates of the invention advantageously has a size typically between 0.1 mm and 1 mm, preferably between 0.2 mm and 1 mm, and in particular between 0.3 mm and 0.8 mm, more generally between 0.4 mm and 0.7 mm, limits inclusive.

The zeolite-based adsorbent in the form of agglomerates according to the present invention advantageously has a high mechanical bulk crushing strength (BCS), measured via the Shell method series SMS1471-74 adapted for agglomerates less than 1.6 mm in size, as described later in the description. The BCS of the zeolite-based adsorbent in the form of agglomerates of the invention is generally greater than or equal to 1.0 MPa, more generally greater than or equal to 1.5 MPa, preferably greater than or equal to 2.0 MPa, typically greater than or equal to 2.1 MPa.

The adsorbent according to the present invention is a zeolite-based material, indicating that it comprises crystals of at least one zeolite, preferably chosen from zeolites of FAU structure chosen especially from zeolites X and Y, and from zeolites of EMT, LTA or MFI structure. Among these zeolites, zeolite X is preferred, without excluding mixtures of zeolite X with one or more of the other zeolites listed above. The Si/Al atomic ratio of the zeolite crystals is advantageously between 1.00 and 1.50, preferably between 1.05 and 1.50 and even more preferably between 1.10 and 1.50, limits inclusive, measured by x-ray fluorescence chemical analysis.

Preferably, the zeolite-based adsorbent of the present invention comprises only one zeolite form, which is zeolite X, identified by XRD, with an Si/Al ratio of between 1.00 and 1.50, preferably between 1.05 and 1.50 and even more preferably between 1.10 and 1.50, limits inclusive, the ratio being measured by x-ray fluorescence chemical analysis.

Advantageously, the zeolite-based adsorbent in the form of agglomerates of the invention comprises more than 90% by weight of zeolite, preferably more than 94% by weight of zeolite(s), very preferably more than 96% by weight of zeolite(s), even more preferably between 96% and 98% by weight of zeolite(s), limits inclusive, relative to the total weight of the zeolite-based adsorbent. The remainder to 100% by weight is constituted by the non-zeolite phase (NZP) especially comprising the unconverted binder or amorphized zeolitized binder, identified by XRD.

According to a preferred embodiment, the zeolite(s) in the zeolite-based adsorbent of the invention are in the form of crystals with a size generally between 10 nm and 1500 nm, preferably between 100 nm and 1200 nm, more preferably between 200 nm and 1100 nm and most particularly preferably between 300 nm and 900 nm, limits inclusive.

In one embodiment, the zeolite-based adsorbent of the present invention has an Si/Al atomic ratio advantageously between 1.00 and 3.00, preferably between 1.00 and 2.00, more preferably between 1.00 and 1.50, limits inclusive, measured by x-ray fluorescence chemical analysis.

Moreover, the zeolite-based adsorbent according to the present invention may contain one or more alkali metals and/or alkaline-earth metals, generally in the form of cations. The alkali metals and/or alkaline-earth metals present are preferably sodium, potassium, barium, and mixtures of two or more thereof in all proportions.

The zeolite-based adsorbent in the form of agglomerates of the present invention also has a specific pore distribution, in which the macropore and mesopore volumes are measured by mercury intrusion and the micropore volume is measured by nitrogen adsorption.

According to a most particularly preferred embodiment of the present invention, the pore distribution of the zeolite-based adsorbent in the form of agglomerates satisfies the inequalities a) and/or b) below:

$$\frac{Vme}{Vme + Vma} \leq 0.1, \qquad \text{a)}$$

preferably $$0.01 \leq \frac{Vme}{Vme + Vma} \leq 0.1,$$

more preferentially $$0.01 \leq \frac{Vme}{Vme + Vma} \leq 0.06;$$

$$0.4 \leq \frac{Vmi}{Vma + Vme + Vmi};\qquad \text{b)}$$

preferably $$0.4 \leq \frac{Vmi}{Vma + Vme + Vmi} \leq 0.6,$$

more preferably $$0.4 \leq \frac{Vmi}{Vma + Vme + Vmi} \leq 0.55.$$

The low tortuosity factor value of the zeolite-based agglomerate according to the present invention allows the most direct possible transportation of molecules through said agglomerate.

According to another aspect, the invention also relates to a process for preparing zeolite-based granular materials as have just been defined, this process comprising at least the following steps:

a) mixing of crystals of at least one zeolite with an agglomeration binder containing at least 80%, preferably at least 90% and more preferably at least 95% by weight of zeolitizable clay, and optionally a source of silica, forming the mixture obtained, and firing at a temperature of between 500° C. to 700° C., for a time advantageously between a few minutes and a few hours, preferably between 2 and 6 hours;

b1) a first step of zeolitization by placing in contact with an alkaline basic solution, with a concentration of between 0.2 M and 0.9 M, preferably between 0.2 M and 0.8 M, limits inclusive;

b2) a second step of zeolitization by placing in contact with an alkaline basic solution, with a concentration of between 1.2 M and 4.0 M, preferably between 1.2 and 3.5 M, more preferably between 1.5 M and 3.5 M and most particularly preferably between 1.5 and 3.0 M, limits inclusive;

steps b1 and b2 possibly being performed in any order and b1 and/or b2 possibly being repeated; preferably, each of the steps b1 and b2 is performed only once;

c) optional cationic exchange of the cations contained in the reaction medium obtained from the zeolitization steps by placing in contact with a solution of barium ions or of barium ions and potassium ions;

d) washing and drying of the zeolite-based agglomerates thus obtained; and e) activation by heating to a temperature generally between 100° C. and 400° C., preferably between 200° C. and 300° C., of the zeolite-based adsorbent in the form of agglomerates obtained in step d).

A sodium hydroxide solution or a mixture of sodium hydroxide and potassium hydroxide may be used as alkaline basic solution for the zeolitization steps. The zeolitization is performed in a minimum of two steps, the concentrations of which are different, the duration of each step advantageously being between a few seconds and several hours, preferably between 30 seconds and 10 hours, each of the zeolitization steps possibly having identical or different durations, as explained later.

Without wishing to be bound by any theory, it would appear that the two zeolitization steps with alkaline basic solutions of different concentration make it possible to obtain adsorbent agglomerates having the required tortuosity factor and porosity. The adsorbents obtained combine both maximum adsorption capacity and improved properties.

The zeolite crystals used in the context of the present invention preferably have a size of greater than or equal to 100 nm and less than or equal to 1500 nm, preferably greater than or equal to 150 nm and strictly less than 1200 nm, and better still greater than or equal to 150 nm and less than or equal to 1100 nm.

As indicated previously, it is preferred to use zeolite crystals of faujasite structure with an Si/Al atomic ratio between 1.00 and 1.50, preferably between 1.05 and 1.50 and even more preferably between 1.10 and 1.50, limits inclusive, measured by x-ray fluorescence chemical analysis.

During step a), besides the zeolite crystals and the agglomeration binder, one or more additives may also be added, for example additives such as silica, especially in the case where the zeolite used is a zeolite X. The possible source of silica may be of any type known to a person skilled in the art, who is a specialist in zeolite synthesis, for example colloidal silica, diatomaceous earths, perlite, fly ash, sand, or any other form of solid silica.

The zeolite crystals used in step a) may thus advantageously be obtained from the synthesis of zeolite X crystals predominantly, or even exclusively, comprising sodium cations, as is the case, for example, for NaX (or 13X) zeolites, but it would not constitute a departure from the scope of the invention to use crystals which have undergone one or more cationic exchanges, between the synthesis in NaX form and its use in step a). In this case, the cationic exchange step d) consequently becomes unnecessary.

The forming operation may make use of an agglomeration binder. According to a preferred embodiment of the invention, said binder comprises at least 80% of a clay or of a mixture of clays, which are optionally zeolitizable, and with up to 5% of additives known to those skilled in the art, for instance, in a nonlimiting manner: carboxymethylcellulose, silica, alumina, and the like, and also with an amount of water allowing forming of the agglomerated material. The zeolite-based adsorbent in the form of agglomerates may thus be formed into a bead, an extrudate or the like, with a size of between 0.1 mm and 1 mm, as indicated previously.

The agglomeration binder used in step a) contains at least 80%, preferably at least 90% and more preferably at least 95% by weight of clay or of mixture of clays from among kaolins, kaolinites, nacrites, dickites, halloysite and/or metakaolins and may contain up to 20%, preferably up to 10% and more preferably up to 5% by weight of one or more additives and/or one or more other mineral binders such as bentonite, attapulgite, sepiolite and the like.

The proportions of agglomeration binder and of zeolite(s) used in step a), and optionally in one or more other subsequent steps, are between 5 parts to 20 parts by weight of agglomeration binder per 95 parts to 80 parts by weight of zeolite(s).

In all the cases, the clays may be used in their raw form or may be subjected beforehand to one or more treatments chosen, for example, from calcination, acid treatment, chemical modification and the like.

As indicated previously, before the zeolitization steps, firing (or "calcination") of the mixture obtained in step a) is performed at a temperature generally between 500° C. and 700° C. The principle thereof is outlined in *Zeolite Molecular Sieves* by D. W. Breck, John Wiley and Sons, New York, (1973), pages 314-315.

The zeolitization steps b1 and b2 by placing in contact with an alkaline basic solution are typically performed by immersing the mixture obtained in step a) in an alkaline basic solution, generally an aqueous solution, for example an aqueous solution of sodium hydroxide and/or potassium hydroxide, the concentrations of which are different, as defined previously.

The zeolitization steps are performed hot or cold, preferably hot, at a temperature above room temperature, and typically between room temperature (i.e. about 20° C.) and the boiling point of the alkaline solution, typically between room temperature and 100° C., preferably between 60° C. and 100° C. and more preferably between 80 and 100° C.

The duration of each zeolitization step is generally between a few seconds and a few hours. In general, a duration of between a few tens of minutes to a few hours, for example between 15 minutes and 8 hours, typically between 30 minutes and 6 hours, is preferred for the zeolitization step at low concentration (step b1 as indicated previously). For the zeolitization step at high concentration (step b2 as indicated previously), a duration of between a few seconds to a few tens of minutes, for example between 30 seconds and 2 hours.

Each of the zeolitization steps is performed with stirring or in the absence of stirring.

It is preferred, however, to perform one or the other, or even the two zeolitization steps, with stirring so as to keep the reaction medium homogeneous.

The intermediate product obtained between each of the zeolitization steps may or may not be isolated. Preferably, the intermediate product is not isolated: the two zeolitization steps are performed one after the other without isolating the intermediate product.

Step c) of optional cation exchange is performed according to the standard methods known to those skilled in the art, and usually by placing the agglomerates obtained from step b) in contact with a salt, such as a chloride, for example barium chloride ($BaCl_2$) for exchange with barium and/or potassium chloride (KCl) for exchange with potassium, in aqueous solution at a temperature between room temperature and 100° C. and preferably between 80° C. and 100° C.

The activation that follows the drying is performed conventionally, according to the methods known to those skilled in the art, for example at a temperature generally between 100° C. and 400° C., preferably between 200° C. and 300° C. The aim of this activation step f) is to fix the water content, and also the loss on ignition of the adsorbent, optimally for the intended use. The process is generally performed by thermal activation, which is preferentially implemented at between 200° C. and 300° C. for a given time as a function of the desired water content and the desired loss on ignition, typically from 1 to 6 hours.

The process of the invention comprises one or forming steps that may be performed according to any technique known to those skilled in the art, for instance extrusion, compacting, agglomeration and the like. It is preferred to perform a single forming step during step a) before firing.

Optionally, one or more additional forming steps may be performed after one or other of the steps a), b), c), d) or e).

The zeolite-based adsorbent in the form of agglomerates according to the invention is particularly suitable for processes for the liquid-phase separation of compounds, and especially for processes in which said material is subjected to high mechanical stresses, for example liquid-phase co-current or counter-current separation processes, and more particularly liquid-phase separation processes in a simulated moving bed. The zeolite-based adsorbent in the form of agglomerates according to the invention is most particularly suitable for liquid-phase xylene separation processes.

The zeolite-based adsorbent according to the invention may also be used:
for the separation of polyhydric alcohols,
for the separation of substituted toluene isomers,
for the separation of cresols.

Thus, and according to yet another aspect, the present invention relates to the use of at least one zeolite-based adsorbent in the form of agglomerates as has just been defined, as adsorbent material in liquid-phase or gas-phase co-current or counter-current separation processes, and more particularly in liquid-phase separation processes in a simulated moving bed, typically in processes for separating aromatic fractions including mixtures of aromatic isomers containing 8 carbon atoms and more particularly in liquid-phase processes for separating xylenes in a simulated moving bed, alone or coupled with a crystallization unit, and most particularly in processes for recovering para-xylene in high purity from aromatic isomer fractions containing 8 carbon atoms.

Finally, the invention also relates to the process for the liquid-phase or gas-phase separation of aromatic fractions including mixtures of isomers containing 8 carbon atoms. The invention relates more particularly to the liquid-phase process for separating xylenes in a simulated moving bed, alone or coupled with a crystallization unit, and most particularly to the process for recovering para-xylene in high purity from aromatic isomer fractions containing 8 carbon atoms, as described, for example, in patent application WO 2009/081024 and in which is used at least one zeolite-based adsorbent in the form of agglomerates as described previously. The process is performed in the presence of a desorbent preferably chosen from toluene and para-diethylbenzene.

The invention also relates to the gas-phase process for separating xylenes in a simulated moving bed, by adsorption of para-xylene using an absorbent as described previously in the presence of a desorbent, preferably chosen from toluene and para-diethylbenzene. Preferably, the process is performed in a simulated moving bed, very preferably in simulated counter-current.

Characterization Techniques

The content of non-zeolite phase, for example non-zeolitized residual binder or any other amorphous phase, after zeolitization is calculated according to the following equation: $NZP=100-\Sigma(ZP)$, ZP represents the sum of the amounts of zeolite X fractions within the meaning of the invention. The amount of zeolite fractions in the zeolite-based adsorbent in the form of agglomerates is measured by x-ray diffraction analysis, known to those skilled in the art by the abbreviation XRD. This analysis is performed on a Brüker machine, and the amount of zeolite fractions ZP and their sum $\Sigma(ZP)$ are evaluated by means of the TOPAS software from the company Brüker. The non-zeolite phase NZP is also evaluated by difference: $NZP=100-\Sigma(ZP)$.

The size of the zeolite crystals in step a) and of the zeolite crystals in the adsorbents is measured by scanning electron microscopy (SEM) observation, by taking a set of images at a magnification of at least 5000. The diameter of at least 200 crystals is then measured using dedicated image analysis software. The accuracy is of the order of 3%.

The zeolite crystals, such as those used in step a) of the process according to the invention, and the zeolite-based adsorbent in the form of agglomerates, are evaluated as regards the Si/Al atomic ratio and the degree of cationic exchange by elemental chemical analysis of the zeolite-based adsorbent, and more precisely by x-ray fluorescence chemical analysis as described in the standard NF EN ISO 12677: 2011 on a wavelength-dispersive spectrometer (WDXRF), for example the Tiger S8 machine from the company Brüker.

The x-ray fluorescence spectrum has the advantage of depending very little on the chemical combination of the element, which offers a precise determination, both quantitatively and qualitatively. A measurement uncertainty of less than 0.4% by weight is obtained conventionally after calibration for each oxide $SiO_2$ and $Al_2O_3$, and also sodium, potassium and barium oxides. The measurement uncertainty of the Si/Al atomic ratio is ±5%.

The determination of the size of the adsorbent is performed by particle size distribution analysis on a sample of agglomerate by imaging according to the standard ISO 13322-2:2006, using a conveyor belt for passing the sample before the objective lens of the camera. The size of the object (number-mean diameter) is then calculated from the particle size distribution by applying the standard ISO 9276-2:2001. The accuracy is of the order of 0.01 mm for the size range of the zeolite-based adsorbent in the form of agglomerates of the invention.

The micropore volume $V_{mi}$ is determined according to any method known to those skilled in the art, for example by measuring the adsorption isotherm of a gas at its liquefaction temperature, for example nitrogen, argon, oxygen and the like. Nitrogen is preferably used. Prior to this adsorption measurement, the zeolite-based adsorbent in the form of agglomerates of the invention is degassed between 300° C. and 450° C. for a time of from 9 hours to 16 hours, under vacuum ($P<6.7\times10^{-4}$ Pa). For example, four a zeolite of FAU structure, measurement of the nitrogen adsorption isotherm at 77 K is then performed on a machine such as ASAP 2020 from Micromeritics, taking at least 35 measurement points at relative pressures of ratio $P/P_0$ between 0.002 and 1. The micropore volume is determined according to the Dubinin-Raduskevitch equation from the isotherm obtained, by applying the standard ISO 15901-3:2007. The micropore volume thus evaluated is expressed in $cm^3$ of liquid adsorbent per gram of anhydrous adsorbent. The measurement uncertainty is ±0.003 g/cm³.

The macropore volume $V_{ma}$ and mesopore volume $V_{me}$, the grain density $d_g$ and the porosity $\varepsilon_p$, of macroporosity and mesoporosity type, are measured by mercury intrusion porosimetry. An Autopore® 9500 mercury porosimeter from Micromeritics is used for analyzing the distribution of the pore volume contained in the macropores and in the mesopores.

The experimental method, described in the machine's operating manual which makes reference to the standard ASTM D 4284-83, consists in placing a sample of adsorbent (zeolite-based adsorbent in the form of agglomerates to be measured) (of known loss on ignition) weighed beforehand, into a porosimeter cell and then, after first degassing (evacuation pressure of 30 μmHg for at least 10 minutes), in filling the cell with mercury to a given pressure (0.0036 MPa) and then in applying a pressure increasing in stages up to 400 MPa in order gradually to make the mercury penetrate into the pore network of the sample, taking at least 15 pressure stages up to 0.2 MPa and then applying increments of 0.1 MPa up to 1 MPa, then 0.5 MPa up to 10 MPa, then 2 MPa up to 30 MPa, then 5 MPa up to 180 MPa, and finally 10 MPa up to 400 MPa.

The relationship between the applied pressure and the characteristic size of the pore inlet threshold (corresponding to an apparent pore diameter) is established using the Laplace-Young equation and by assuming a cylindrical pore aperture, a contact angle between the mercury and the wall of the pores of 140° and a mercury surface tension of 485 dynes/cm. The volume increments $\Delta Vi$ of mercury introduced at each pressure stage Pi are recorded, which then makes it possible to plot the cumulative volume of mercury introduced as a function of the applied pressure V(Pi), or as a function of the apparent pore diameter V(Ii). The value from which the mercury fills all the inter-granular voids is set at 0.2 MPa, and it is considered that beyond this value, the mercury penetrates into the pores of the adsorbent. The grain volume Vg is then calculated by subtracting the cumulative volume of mercury at this pressure (0.2 MPa) from the volume of the porosimeter cell, and by dividing this difference by the mass of the anhydrous equivalent adsorbent, i.e. the mass of said material corrected for the loss on ignition. The grain density dg is the inverse of the grain volume Vg defined previously.

The macropore volume Vma of the adsorbent is defined as being the cumulative volume of mercury introduced at a pressure of between 0.2 MPa and 30 MPa, corresponding to the volume contained in the pores with an apparent diameter of greater than 50 nm. The mesopore volume Vme of the adsorbent is defined as being the cumulative volume of mercury introduced at a pressure of between 30 MPa and 400 MPa. Since the method for measuring the pore volume by mercury intrusion does not make it possible to gain access to the micropore volume, the total pore volume $V_{tot}$ as measured by mercury intrusion corresponds to the sum of the macropore volume $V_{ma}$ and of the mesopore volume $V_{me}$.

In the present document, the macropore and mesopore volumes $V_{ma}$ and $V_{me}$, and the sum thereof (total pore volume $V_{tot}$), of the zeolite-based adsorbents, expressed in $cm^3 \cdot g^{-1}$, are thus measured by mercury intrusion porosimetry and related to the mass of the sample as anhydrous equivalent, i.e. the mass of said adsorbent corrected for the loss on ignition. The grain density $d_g$ is expressed in $g \cdot cm^{-3}$ and refers to the mass of the sample as anhydrous equivalent.

The porosity $\varepsilon_p$ of macroporosity and mesoporosity type is the product of the grain density $d_g$ by the sum of the macropore and mesopore volumes Vma and Vme: $\varepsilon_p = d_g \times (V_{ma}+V_{me})$.

The tortuosity factor τ is determined via a standard measurement detailed in the Autopore® machine user's manual and modified for the case of microporous materials. The measurement is based on the following equation obtained from Carniglia in "Construction of the tortuosity factor from porosimetry" J. of Catalysis 102, 401-418 (1986)):

$$\tau = (2.23 - 1,13 \cdot V_{tot} \cdot d_g)\left(0,92 \frac{4}{S_S} \sum_{Pi=0,2MPa}^{Pdc} \frac{\Delta Vi}{li}\right)^{1+\delta} \quad \text{equation 2}$$

The parameters δ and $S_s$ are two user parameters:

δ is an exponent reflecting the diffusion mechanism: it is equal to 0 or 1 depending on whether the transportation properties of the zeolite-based adsorbents are evaluated for their use in liquid-phase or gas-phase processes, respectively.

$S_s$ is the surface area of the pores of macropore and mesopore type, expressed in m² per gram of sample as anhydrous equivalent. The user's manual suggests assigning to the parameter $S_s$ the value of the BET specific surface area measured by nitrogen adsorption porosimetry. However, in the case of the materials according to the invention, obtained by agglomeration of individual zeolite crystals, the BET specific surface area integrates not only the surface area of the pores of macropore and mesopore type, but also an equivalent surface area representing adsorption in the micropores. In the present invention, the tortuosity factor is thus determined using a user parameter $S_s$ adapted to cases of agglomerates of zeolite structure in the following manner: the parameter $S_s$ may be likened to the outer surface area of the constituent crystals of the adsorbent relative to their mass. For faujasite zeolite crystals, for which the ratio of the volume to the outer surface area is supposed to be equal to the diameter of the crystals divided by 6 (same ratio as for a sphere), the surface area parameter $S_s$ is calculated according to equation 3 below:

$$S_S = \frac{6 \cdot V_{mi}}{f \cdot d_{crystals}} \quad \text{equation 3}$$

in which f is the void fraction in the crystals, and $d_{crystals}$ is the number-mean diameter of the zeolite crystals of the zeolite-based adsorbent measured by observation with a scanning electron microscope (SEM). The value of f is taken as equal to 0.5 in the case of an NaX zeolite with an Si/Al ratio=1.25 (Table 5.9, page 429 of the book *Zeolite Molecular Sieves* by de D. W. Breck, John Wiley and Sons, New York, (1973)) and this value will be conserved in the case of the zeolite-based adsorbent after exchange of the sodium cations with barium and/or potassium cations, since this volume ratio is not modified during exchange with cations of this type.

in equation 2, the sum is done for mercury intrusion pressures of between 0.2 MPa and a pressure Pdc corresponding to an apparent pore inlet threshold diameter Idc equal to:

Idc=25 times the molecular radius of the molecules that will be transported in the zeolite-based adsorbent for use in the separation of a liquid mixture, i.e. 17 nm in the case of the invention applied to xylene molecules, i.e. a pressure Pdc equal to 87 MPa.

Idc=5 times the mean free path of the gas in the zeolite-based adsorbent for use in the separation of a gaseous mixture.

The mechanical strength measured is the bulk crushing strength (BCS) characterized according to the Shell method series SMS1471-74 (Shell Method Series SMS1471-74 *Determination of Bulk Crushing Strength of Catalysts. Compression-Sieve Method*), associated with the BCS Tester machine sold by the company Vinci Technologies.

This method for measuring the BCS, initially intended for characterizing catalysts of 3 mm to 6 mm, is based on the use of a 425 µm screen, which will make it possible especially to separate the fines created during the crushing. The use of a 425 µm screen remains suitable for particles with a diameter of greater than 1.6 mm, but should be adapted according to the particle size of the material that it is desired to characterize. For the zeolite-based adsorbent in the form of agglomerates of the present invention, a 200 µm screen is used instead of the 425 µm screen mentioned in the standard Shell method SMS1471-74.

The measuring protocol is as follows: a sample of 20 cm³ of material to be analyzed, prescreened with the appropriate screen (200 µm) and predried in an oven for at least 2 hours at 250° C. (instead of 300° C. mentioned in the standard Shell method SMS1471-74), is placed in a metal cylinder of known internal cross section. An increasing force is imposed in stages on this sample by means of a piston, through a bed of 5 cm³ of steel beads so as better to spread the force exerted by the piston on the material (use of beads 2 mm in diameter for particles of spherical shape with a diameter strictly less than 1.6 mm). The fines obtained at the various pressure stages are separated out by screening (suitable screen of 200 µm) and weighed.

EXAMPLES

The BCS is determined by the pressure in megapascals (MPa) for which the amount of cumulative fines passing through the screen is 0.5% by weight of the sample. This value is obtained by plotting on a graph the mass of fines obtained as a function of the force applied to the bed of zeolite-based material and by interpolating to 0.5% by mass of cumulative fines. The mechanical bulk crushing strength is typically between a few hundred kPa and a few tens of MPa and generally between 0.3 MPa and 3.2 MPa. The accuracy is conventionally less than 0.1 MPa.

The examples that follow illustrate the subject of the invention. They are provided purely as guides and are not in any way intended to limit the various embodiments of the present invention.

Example A

Preparation of Zeolite-Based Adsorbents Based on Zeolite X

Synthesis of Zeolite X Crystals with an Si/Al Atomic Ratio=1.25, a Number-Mean Diameter of 1.0 µm and an Na/Al Atomic Ratio=1

A gel of molar composition 3.5 $Na_2O$-2.8 $SiO_2$—$Al_2O_3$-130 $H_2O$ is prepared by mixing the following reagents: sodium silicate, sodium aluminate and water. The gel is matured at 35° C. for 20 hours, and crystallization takes place for 4 hours at 100° C.

The crystals obtained after filtration and washing are identified by x-ray diffraction (XRD analysis) as being faujasite crystals. Chemical analysis of the solid gives an Si/Al atomic ratio=1.25. The micropore volume evaluated by means of the Dubinin-Raduskevitch equation as described in the technical characterization section and expressed in cm³ per gram of dry adsorbent is 0.345±0.003 cm³/g. Analysis of the size of the zeolite crystals is performed by scanning electron microscopy and shows that their number-mean diameter ($d_{crystals}$) is 1.0 µm.

Preparation of the Zeolite-Based Adsorbents

A homogeneous mixture is prepared and 800 g of crystals of NaX zeolite prepared according to the procedure described above are agglomerated with 105 g of kaolin (expressed as calcined equivalent) and 45 g of colloidal silica sold under the trade name Klebosol™ 30N50 (containing 30% by weight of $SiO_2$ and 0.5% by weight of $Na_2O$) with the amount of water allowing extrusion of the mixture. The extrudates are dried and then calcined at 550° C. (firing of the clay) under a stream of nitrogen for 2 hours, and finally crushed so as to recover agglomerates whose number-mean diameter is equal to 0.5 mm.

Example 1 (Comparative)

20 g of agglomerates obtained as described above from crystals of zeolite X synthesized in example A are placed in a glass reactor equipped with a jacket regulated at a temperature of 100° C.±1° C., and 150 mL of an aqueous sodium hydroxide solution of concentration 2.5 M are then added and the reaction medium is left stirring for a time of 4 to 5 hours.

The agglomerates are then washed in three successive operations of washing with water followed by emptying the reactor. The washing efficiency is ensured by measuring the final pH of the washing waters, which is between 10.0 and 10.5.

These agglomerates are exchanged by placing in contact with a 0.5 M barium chloride solution at 95° C. in 4 steps. At each step, the ratio of the volume of solution to the mass of solid is 20 mL/g and the exchange is continued for 4 hours each time. Between each exchange, the solid is washed several times so as to free it of the excesses of salt. The agglomerates are then dried at 80° C. for 2 hours and finally activated at 250° C. for 2 hours under a stream of nitrogen.

The pore distribution and the mechanical strength (BCS) of the agglomerates are characterized via the characterization techniques described above. The results are given in Table 1 below. The porosity values $\varepsilon_p$, calculated according to equation 2 taking $\delta=0$, and the tortuosity factor values $\tau$ are given in table 2 below.

The degree of barium exchange of the agglomerates calculated from the elemental analyses of the barium and sodium oxides by x-ray fluorescence, as described in the characterization techniques, is 99.6±0.2%. The loss on ignition measured as described previously is 5.2%±0.1%.

Example 2 (According to the Invention)

1$^{st}$ Step:
20 g of agglomerates obtained from the powder synthesized in example A are placed in a glass reactor equipped with a jacket regulated at a temperature of 100° C.±1° C., 100 mL of an aqueous sodium hydroxide solution of concentration 0.5 M are then added and the reaction medium is left stirring for 3 hours.

2$^{nd}$ Step:
After 3 hours, 100 mL of a 5.5 M solution of sodium hydroxide prepared beforehand and maintained at a temperature of 100° C.±1° C. are added to this solution so as to obtain a sodium hydroxide concentration equal to 3M in the reaction medium. The reaction medium is left stirring for 1 hour.

The agglomerates are then washed in three successive operations of washing with water followed by emptying the reactor. The washing efficiency is ensured by measuring the final pH of the washing waters, which generally remains between 10.0 and 10.5.

These agglomerates are engaged in a cationic exchange reaction by placing in contact with aqueous 0.5 M barium chloride solution at 95° C. in 4 steps. At each step, the ratio of the volume of solution to the mass of solid is 20 mL/g and the exchange is continued for 4 hours each time. Between each exchange, the solid is washed several times so as to free it of the excesses of salt, for example 4 washes of 50 mL of water. The agglomerates are then dried at 80° C. for 2 hours and finally activated at 250° C. for 2 hours under a stream of nitrogen.

The products are characterized so as to determine via all the analytical techniques described above: the Dubinin-Raduskevitch volume is 0.260 cm$^3$/g and the BCS is 3.1 MPa.

The loss on ignition measured as described previously is 5.2%±0.1% for each sample. The degree of barium exchange of the agglomerates calculated from the elemental analyses of the barium and sodium oxides by x-ray fluorescence, as described in the characterization techniques, is 99.4±0.2%.

TABLE 1

| | BCS (MPa) | Vg (cm$^3$/g) | Vmi (cm$^3$/g) | Vme (cm$^3$/g) | Vma (cm$^3$/g) | Vme/ (Vme + Vma) | Vmi/ (Vmi + Vme + Vma) |
|---|---|---|---|---|---|---|---|
| Example 1 (comparative) | 2.62 | 0.840 | 0.258 | 0.014 | 0.261 | 5.1% | 48% |
| Example 2 (according to the invention) | 3.10 | 0.800 | 0.260 | 0.008 | 0.212 | 3.5% | 55% |

TABLE 2

| | Surface area parameter $S_s$ of equation 2 (calculated by equation 3 with f = 0.5) | Tortuosity factor $\tau$ (equation 2 with $\delta$ = 0 and Pdc = 87 MPa) | Porosity $\varepsilon p$ |
|---|---|---|---|
| Example 1 (comparative) | 3.3 | 3.2 | 32% |
| Example 2 (according to the invention) | 3.5 | 2.1 | 28% |

Example 3

Xylene Separation Test (Breakthrough Test)

A breakthrough test (frontal chromatography) is then performed on the adsorbents described in examples 1 and 2 to evaluate their efficiency. The amount of adsorbent used for these tests is 72 g.

The procedure for obtaining the breakthrough curves is as follows:
Filling of the column with the sieves and insertion in the test bench.

Filling with the solvent (para-diethylbenzene) at room temperature.

Gradual increase to the adsorption temperature under a stream of solvent (5 cm³/min).

injection of solvent at 20 cm³/min when the adsorption temperature is reached.

Solvent/feedstock permutation to inject the feedstock (20 cm³/min).

The injection of the feedstock is then maintained until the solvent concentration in the effluent is zero, so as to reach thermodynamic equilibrium.

The pressure is sufficient for the feedstock to remain in liquid phase, i.e. 1 MPa. The adsorption temperature is 175° C.

The composition of the feedstock is as follows:
para-Xylene: 45% by weight
meta-Xylene: 45% by weight
Isooctane: 10% by weight (this is used as a tracer for estimating the non-selective volumes and does not participate in the separation).

TABLE 3

| Nature of the solid | LOI[1] at 950° C. | Capacity[2] | Selectivity[3] $\alpha_{PX/MX}$ | HEPT iC8[4] | HEPT PX[5] |
|---|---|---|---|---|---|
| Ex. 1 (comparative) | 5.2% | 0.211 | 3.57 | 3.3 | 7.1 |
| Ex. 2 | 5.2% | 0.218 | 3.63 | 2.8 | 6.1 |

[1] LOI: Loss on ignition
[2] The capacity is expressed in cm³ of C8 aromatics adsorbed per gram of adsorbent
[3] PX = para-Xylene, MX: meta-Xylene
[4] HEPT iC8: Theoretical plate height expressed in cm of the isooctane breakthrough front
[5] HEPT PX: Theoretical plate height expressed in cm of the para-xylene breakthrough front The results of table 3 show that the agglomerates according to the invention lead to a lower theoretical plate height and in fact to better productivity and greater purity of the expected product.

Example 4 (Comparative)

1st Step:
20 g of agglomerates obtained from the powder synthesized in example A are placed in a glass reactor equipped with a jacket regulated at a temperature of 100° C.±1° C., 200 mL of an aqueous sodium hydroxide solution of concentration 0.5 M are then added and the reaction medium is left stirring for 4 hours.

The agglomerates are then washed in three successive operations of washing with water followed by emptying the reactor. The washing efficiency is ensured by measuring the final pH of the washing waters, which generally remains between 10.0 and 10.5.

These agglomerates are engaged in a cationic exchange reaction by placing in contact with aqueous 0.5 M barium chloride solution at 95° C. in 4 steps. At each step, the ratio of the volume of solution to the mass of solid is 20 mL/g and the exchange is continued for 4 hours each time. Between each exchange, the solid is washed several times so as to free it of the excesses of salt, for example 4 washes of 50 mL of water. The agglomerates are then dried at 80° C. for 2 hours and finally activated at 250° C. for 2 hours under a stream of nitrogen.

The products are characterized. The Dubinin-Raduskevitch volume is 0.250 cm³/g.

Example 5 (Comparative)

1st Step:
20 g of agglomerates obtained from the powder synthesized in example A are placed in a glass reactor equipped with a jacket regulated at a temperature of 100° C.±1° C., 200 mL of an aqueous sodium hydroxide solution of concentration 3 M are then added and the reaction medium is left stirring for 4 hours.

The agglomerates are then washed in three successive operations of washing with water followed by emptying the reactor. The washing efficiency is ensured by measuring the final pH of the washing waters, which generally remains between 10.0 and 10.5.

These agglomerates are engaged in a cationic exchange reaction by placing in contact with aqueous 0.5 M barium chloride solution at 95° C. in 4 steps. At each step, the ratio of the volume of solution to the mass of solid is 20 mL/g and the exchange is continued for 4 hours each time. Between each exchange, the solid is washed several times so as to free it of the excesses of salt, for example 4 washes of 50 mL of water. The agglomerates are then dried at 80° C. for 2 hours and finally activated at 250° C. for 2 hours under a stream of nitrogen.

The products are characterized. The Dubinin-Raduskevitch volume is 0.240 cm³/g.

TABLE 4

| | Surface area parameter $S_s$ of equation 2 (calculated by equation 3 with f = 0.5) | Tortuosity factor $\tau$ (equation 2 with $\delta$ = 0 and Pdc = 87 MPa) | Porosity $\epsilon p$ |
|---|---|---|---|
| Example 4 (comparative) | 3.2 | 3.3 | 36% |
| Example 5 (comparative) | 3.1 | 3.4 | 36% |

The invention claimed is:

1. A zeolite-based adsorbent in the form of agglomerates, said adsorbent having:

a tortuosity factor $$t == (2.23 - 1,13 \cdot v_{tot} \cdot d_g)\left(0,92 \frac{4}{S_s} \sum_{Pi=0,2MPa}^{Pdc} \frac{\Delta Vi}{li}\right)^{1+\delta}$$

calculated from the pore distribution determined by mercury intrusion porosimetry, strictly greater than 1 and strictly less than 3, in which Vtot is the total porous volume: sum of macroporous and mesoporous volumes expressed in cm³·g⁻¹; $\delta$=0 for liquid phase or 1 for gas-phase; Ss is the surface area of the pores of macropore and mesopore type, expressed in m² per gram of sample as anhydrous equivalent; $\Delta$Vi is the mercury incremental volume; dg is the grain density expressed in g·cm⁻³; Pdc=87 MPa; and a porosity $$e_p = \frac{Vma + Vme}{Vg},$$

determined by mercury intrusion porosimetry, in which $V_{ma}$ denotes the macropore volume, $V_{me}$ denotes the mesopore volume and Vg denotes the grain volume, of between 25% and 35%, the volumes being expressed in cm³·g⁻¹.

2. The zeolite-based adsorbent as claimed in claim 1, in which the tortuosity factor t is between 1.5 and 2.7.

3. The zeolite-based adsorbent as claimed in claim 1, wherein the high mechanical bulk crushing strength (BCS), measured via the Shell method series SMS1471-74 adapted for agglomerates less than 1.6 mm in size, is greater than or equal to 1.0 MPa.

4. The zeolite-based adsorbent as claimed claim 1, wherein said adsorbent has a size of between 0.1 mm and 1 mm, limits inclusive.

5. The zeolite-based adsorbent as claimed in claim 1, wherein said adsorbent comprises a zeolite chosen from the zeolites of FAU structure.

6. The zeolite-based adsorbent as claimed in claim 5, said zeolite being zeolite X, alone or as a mixture with zeolites chosen from among zeolites Y, EMT, LTA and MFI.

7. The zeolite-based adsorbent as claimed in claim 1, wherein said adsorbent comprises more than 90% by weight of zeolite.

8. The zeolite-based adsorbent as claimed in claim 1, wherein said zeolite is in the form of crystals between 10 nm and 1500 nm in size.

9. The zeolite-based adsorbent as claimed in claim 1, wherein the pore distribution satisfies the inequalities a) and/or b) below:

$$\frac{Vme}{Vme + Vma} \leq 0.1, \quad \text{a)}$$

$$0.4 \leq \frac{Vmi}{Vma + Vme + Vmi} \quad \text{b)}$$

Vmi denoting the micropore volume expressed in $cm^3 \cdot g^{-1}$, determined by nitrogen adsorption.

10. The zeolite-based adsorbent as claimed in claim 1, further comprising barium and/or potassium.

11. A process for preparing a zeolite-based adsorbent as claimed in claim 1, comprising at least following steps:
   a) a step of mixing crystals of at least one zeolite with an agglomeration binder containing at least 80 of zeolitizable clay, and optionally a source of silica, followed by forming and a firing step at a temperature of between 500 and 700° C.,
   b1) a first step of zeolitization by placing the material obtained in step a) in contact with an alkaline basic solution, with a concentration of between 0.2 M and 0.9 M, limits inclusive,
   b2) a second step of zeolitization by placing the material obtained in step b1) in contact with an alkaline basic solution, with a concentration of between 1.2 M and 4.0 M, limits inclusive,
   b1 and b2 possibly being performed in any order and b1 and/or b2 possibly being repeated,
   c) an optional step of cationic exchange of the cations contained in the reaction medium obtained from the zeolitization steps by placing in contact with a solution of barium ions or of barium ions and potassium ions,
   d) a step of washing and drying the material thus obtained, and
   e) a step of activation of the material obtained in step d), by heating to a temperature of between 100° C. and 400° C., and recovery of the zeolite-based adsorbent in the form of agglomerates.

12. The process as claimed in claim 11, further comprising a step of extruding the zeolite-based adsorbent to an agglomerated form and/or compacting the material formed after any one of steps a), b1)/b2), c), d) or e).

13. A process for separating para-xylene from aromatic hydrocarbon isomer fractions containing 8 carbon atoms, in the liquid phase, comprising selectively adsorbing the para-xylene onto the adsorbent as claimed in claim 1 by contacting a mixture of the para-xylene and the aromatic hydrocarbon isomer fractions containing 8 carbon atoms with the adsorbent, in the presence of a desorbent.

14. A process for separating para-xylene from aromatic hydrocarbon isomer fractions containing 8 carbon atoms, in the gaseous phase, comprising selectively adsorbing the para-xylene onto the adsorbent as claimed in claim 1 by contacting a mixture of the para-xylene and the aromatic hydrocarbon isomer fractions containing 8 carbon atoms with the adsorbent, in the presence of a desorbent.

15. The process as claimed in claim 13, wherein the contacting is conducted in a simulated moving bed column.

16. The process as claimed in claim 14, wherein the contacting is conducted in a simulated moving bed column.

* * * * *